United States Patent
Rogers et al.

(10) Patent No.: US 6,482,188 B1
(45) Date of Patent: Nov. 19, 2002

(54) NONVENTED NEEDLE-FREE INJECTION VALVE

(75) Inventors: Bobby E. Rogers, San Diego, CA (US); Kevin S. Nason, Menlo Park, CA (US); Gino Kang, Newport Beach, CA (US)

(73) Assignee: Mission Medical Devices, Inc., San Diego, CA (US)

(*) Notice: Subject to any disclaimer, the term of this patent is extended or adjusted under 35 U.S.C. 154(b) by 0 days.

(21) Appl. No.: 10/023,195

(22) Filed: Dec. 17, 2001

Related U.S. Application Data

(63) Continuation-in-part of application No. 09/410,419, filed on Oct. 1, 1999.

(51) Int. Cl.[7] ............................. A61M 5/00; F16L 37/28
(52) U.S. Cl. .................................... 604/249; 251/149.6
(58) Field of Search ................................ 604/246, 249, 604/256, 523, 537, 539, 284, 950; 251/149.1, 149.6; 137/843

(56) References Cited

U.S. PATENT DOCUMENTS

| | | |
|---|---|---|
| 3,570,484 A | 3/1971 | Steer |
| 3,831,629 A | 8/1974 | Mackal et al. |
| 3,965,910 A | 6/1976 | Fischer |
| 4,429,856 A | 2/1984 | Jackson |
| 4,668,215 A | 5/1987 | Allgood |
| 4,683,916 A | 8/1987 | Raines |
| 4,991,820 A | 2/1991 | Kohn et al. |
| 5,006,114 A | 4/1991 | Rogers et al. |
| 5,049,128 A | 9/1991 | Duquette |
| 5,147,333 A | 9/1992 | Raines |
| 5,184,652 A | 2/1993 | Fan |
| 5,201,725 A | 4/1993 | King |
| 5,242,432 A | 9/1993 | DeFrank |
| 5,279,579 A | 1/1994 | D'Amico |
| 5,284,475 A | 2/1994 | Mackal |
| 5,347,992 A | 9/1994 | Pearlman et al. |
| 5,353,837 A * | 10/1994 | Faust ........................ 604/249 |
| 5,360,413 A | 11/1994 | Leason et al. |
| 5,439,451 A * | 8/1995 | Collinson et al. ........... 604/247 |
| 5,578,059 A | 11/1996 | Petzer |
| 5,730,418 A | 3/1998 | Feith et al. |
| 5,776,113 A | 7/1998 | Daugherty et al. |
| 5,820,601 A | 10/1998 | Mayer |
| 5,836,923 A | 11/1998 | Mayer |
| 5,921,264 A | 7/1999 | Paradis |
| 6,029,946 A | 2/2000 | Doyle |
| 6,048,335 A | 4/2000 | Mayer |
| 6,050,978 A | 4/2000 | Orr et al. |
| 6,228,069 B1 * | 5/2001 | Barth et al. .................. 604/249 |
| 6,245,048 B1 | 6/2001 | Fangrow, Jr. et al. |
| 6,290,206 B1 | 9/2001 | Doyle |
| 6,299,131 B1 | 10/2001 | Ryan |
| 6,299,132 B1 | 10/2001 | Weinheimer |

* cited by examiner

*Primary Examiner*—Anhtuan T. Nguyen

(57) ABSTRACT

An injection valve includes a housing having an inlet, an outlet, and a fluid channel extending between the inlet and the outlet. A piston is slidable within a bore of the housing between a first position wherein the piston is relatively far from the closed end and a second position wherein the piston is relatively near to the closed end. A biasing spring biases the piston toward the first position. The piston closes and seals the inlet when the piston is in the first position and allows fluid to pass from the inlet to the fluid channel to the outlet when the piston is in the second position. A piston seal is formed between the piston and a wall of the bore, dividing the bore into a unsealed chamber and a sealed chamber adjacent to the closed end. There is no vent between the sealed chamber and an exterior of the housing. Pressure differences between the unsealed chamber and the sealed chamber that adversely affect performance may be minimized by providing a deformable membrane or a gas accumulator communicating with the sealed chamber, or providing an initial pressure differential wherein a gas pressure within the sealed chamber is less than a gas pressure within the unsealed chamber, when the piston is in its first position.

16 Claims, 3 Drawing Sheets

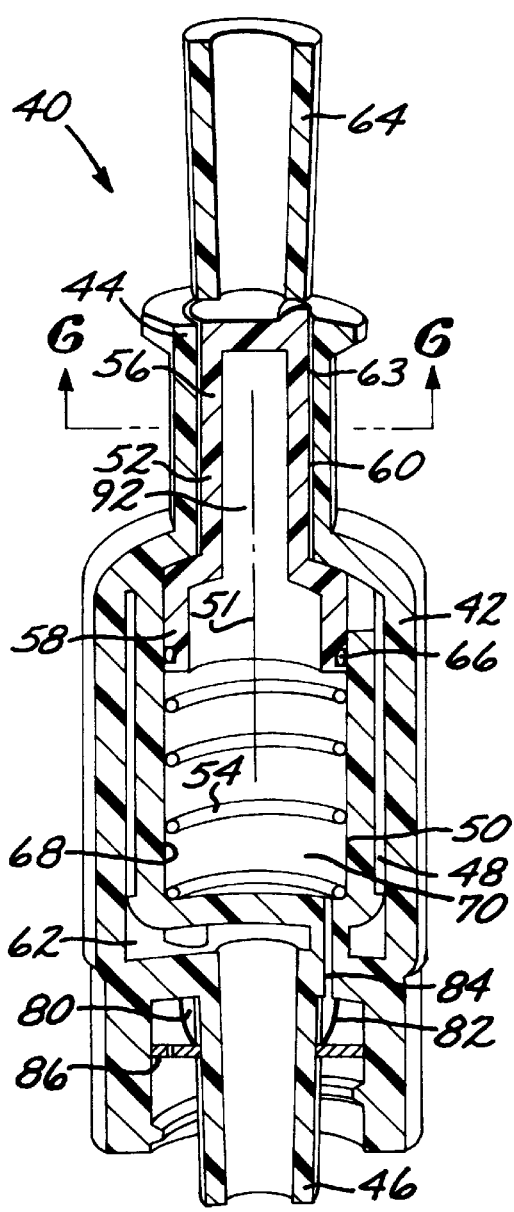
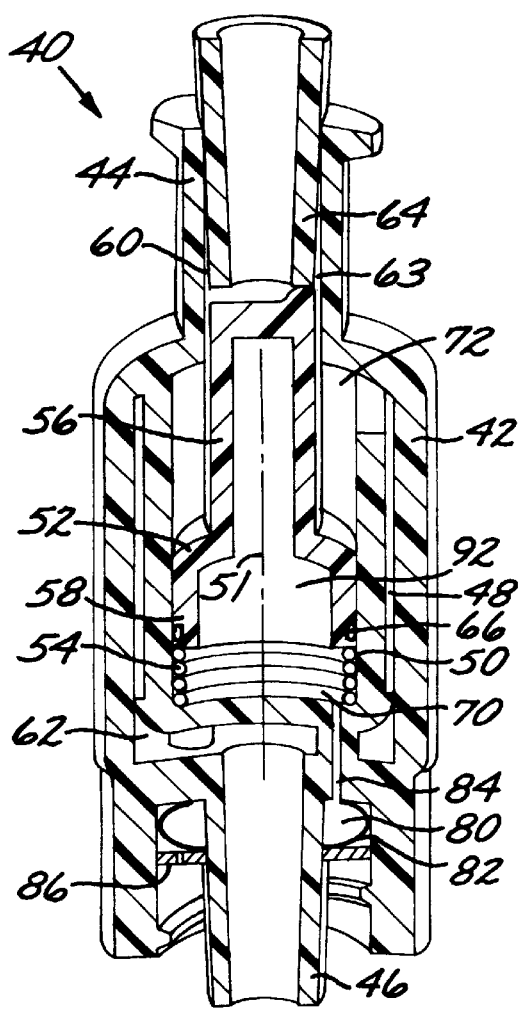
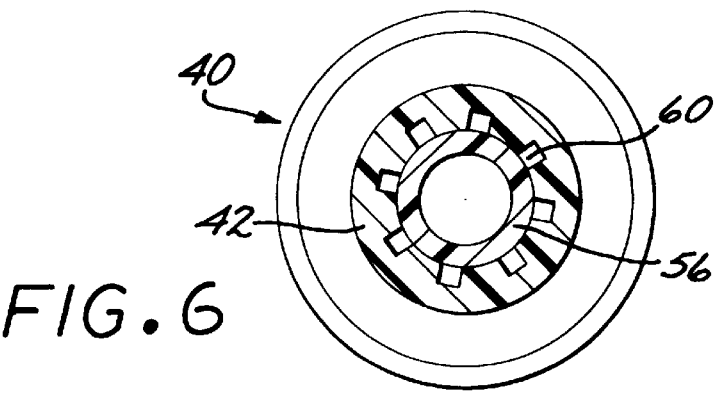

NONVENTED NEEDLE-FREE INJECTION VALVE

This application is a continuation-in-part of pending application Ser. No. 09/410,419, filed Oct. 1, 1999, for which priority is claimed and whose disclosure is incorporated by reference.

This invention relates to needle-free injection devices and, more particularly, to a needle-free injection device that avoids potential contamination of the injected fluids.

BACKGROUND OF THE INVENTION

Needles were originally used in the common medical practice of intravenously infusing various liquids into a blood vessel of a patient, performing series of injections into patients, taking blood samples, and the like. Needles, however, present a risk of passing blood borne pathogens to health care providers should they be inadvertently stuck by a used needle. Needle-free injection sites or valves were developed to eliminate the problems associated with the use of needles in medical procedures. The nature of the problem and the use of needle-free injection valves are discussed more fully in U.S. Pat. No. 5,006,114, whose disclosure is incorporated by reference. The '114 patent also discusses several ways in which a connector may be made to eliminate the use of the needle.

Briefly, there are at least three major types of needle-free devices. The first is the split septum-type connector, which is accessed by a blunt cannula. The second is a sheathed needle. The third is a valve-type mechanism in which a standard male-to-female medical luer-friction connection is made between the outlet side of a syringe and the inlet side of a needle-free valve. When this connection is made, a piston is displaced from a closed to an open position, thereby allowing fluid to flow through the valve to the output side of the valve. The outlet side of the valve is connected through a male-to-female luer connection to a catheter that has been set in the patient. Once the fluid has been administered to the patient, the syringe is disconnected from the valve and the piston returns to its closed position to seal the injection valve. Examples of such valve-type mechanisms are found in U.S. Pat. Nos. 6,228,069; 6,245,048; and 5,439,451.

While such valve-type mechanisms provide an improvement over alternative approaches, the available valve-type mechanisms permit contamination of the sterile fluid being injected into the patient, with potentially highly injurious or even fatal results. There is a need for an improved approach to needle-free injection valves which avoid inadvertently drawing fluid out of the patient as a result of the deactivation of the valve, and also avoid contamination of the sterile fluid being injected. The present invention fulfills this need, and further provides related advantages.

SUMMARY OF THE INVENTION

The present invention provides a nonvented, needle-free injection valve. No needle is used in the valve or in the syringe used in the injection procedure. The needle-free injection valve includes a fluid capacitor that prevents injected fluid or bodily fluids from being drawn out of the injection location in the patient. The needle-free injection valve is sealed against intrusion of external fluids or gases into the interior of the valve, avoiding contamination of the sterile fluid being injected.

In accordance with the invention, an injection valve comprises a housing having an inlet, an outlet, and a fluid channel extending between the inlet and the outlet, and a bore within the housing. A piston is slidable within the bore between a first position and a second position and biased toward the first position. The piston closes and seals the inlet when the piston is in the first position, and allows fluid to pass from the inlet to the fluid channel to the outlet when the piston is in the second position. There is a piston seal between the piston and a wall of the bore. The piston seal divides the bore into a sealed chamber and an unsealed chamber. There is no vent between the sealed chamber and an exterior of the housing. Desirably, the bore is substantially cylindrical with a bore axis, and the inlet and the outlet are coaxial along the bore axis. The piston seal is preferably a sliding seal but it may be a diaphragm-type or other type of seal.

In an injection operation, the piston is initially in the first position and seals the inlet. To inject a sterile fluid into a patient, an end of a (needleless) syringe is inserted into the inlet, pushing the piston to the second position and unsealing the inlet. The syringe is operated to inject sterile fluid into the inlet, through the fluid channel, and out the outlet to a catheter inserted into the patient. Fluid enters the unsealed chamber during this injection procedure. When the injection is complete, the end of the syringe is withdrawn from the inlet. The piston moves back to the first position and seals the inlet. As the piston moves from the second position to the first position, sterile fluid is forced from the unsealed chamber through the fluid channel and out the outlet to the patient, preventing bodily fluids from being drawn out of the patient and back into the catheter and the injection valve. The injection valve works much the same for an aspiration, in which the inserted syringe end creates a partial suction to take blood from the patient through the catheter. In each case, it is conventional practice to inject a small amount of saline both prior to and after a fluid injection or aspiration.

In another embodiment, an injection valve comprises a housing having an inlet, an outlet, a fluid channel extending between the inlet and the outlet, and a bore within the housing, the bore having a closed end. A piston is slidable within the bore between a first position wherein the piston is relatively far from the closed end and a second position wherein the piston is relatively near to the closed end. The piston closes and seals the inlet when the piston is in the first position and allows fluid to pass from the inlet to the fluid channel to the outlet when the piston is in the second position. A biasing spring biases the piston toward the first position. A piston seal between the piston and a wall of the bore divides the bore into an unsealed chamber and a sealed chamber adjacent to the closed end. There is no vent between the sealed chamber and an exterior of the housing. Features discussed in relation to the other embodiments may be used with this embodiment.

In one version of this embodiment, a deformable membrane has a first side in communication with the sealed chamber. The deformable membrane is deformable responsive to gas pressure changes within the sealed chamber. In another version, a gas accumulator communicates with the sealed chamber. In another version, a gas pressure within the sealed chamber is less than a gas pressure within the unsealed chamber, when the piston is in its first position. These embodiments minimize any adverse affect on piston movement arising from the compression of the gas in the sealed chamber.

In a third embodiment, an injection valve comprises a housing having a body, an inlet tube at a first end of the body, an outlet tube at a second end of the body remote from the first end, and a fluid channel extending through the body and between the inlet tube and the outlet tube. Preferably, the inlet tube is sized to receive a syringe tip therein. There is a bore within the housing. The bore has a bore axis and a closed end adjacent to the second end of the body. The inlet tube is coaxial with the bore axis. A piston has a first axial segment coaxial with the bore axis and slidable within the bore between a first position wherein the first axial segment is relatively far from the closed end and a second position wherein the first axial segment is relatively near to the closed end. The piston further has a second axial segment coaxial with the bore axis and remote from the closed end of the bore. The second axial segment closes and seals the inlet tube when the first axial segment is in the first position and allows fluid to pass through the inlet tube when the first axial segment is in the second position. A biasing spring biases the piston toward the first position. A piston seal is positioned between the first axial segment of the piston and a wall of the bore. The piston seal divides the bore into a unsealed chamber and a sealed chamber adjacent to the closed end. There is no vent between the sealed chamber and an exterior of the housing. In all of the embodiments and versions, it is preferred that the inlet and the outlet are coaxial with the bore axis. Other features discussed in relation to the prior embodiment may be used with this embodiment.

In prior designs of needle-free injection valves, a vent is provided through the housing between the otherwise-sealed chamber defined at the otherwise-closed end of the bore, and the exterior of the housing. The resulting venting equilibrates the pressure in the sealed chamber and the external environment to minimize the possibility that gas could flow past the piston seal and into the fluid being injected. Thus, the vent is used to maintain ambient pressure in the sealed chamber to prevent gas from being driven across the piston seal and into the unsealed chamber. The pressure equilibration also avoids a back pressure on the piston that can interfere with its operation and makes the valves easier to operate. However, the presence of the vent creates other problems which have either not been appreciated or have been ignored as having no apparent solution. The vent is typically located in a relatively inaccessible location where it cannot be readily disinfected. Nonsterile gases or fluids from the external environment, and microorganisms that they carry, may enter the interior of the valve through the vent. Even though there is a sliding seal between the piston and the wall of the bore to define the sealed chamber, the nonsterile gases or fluids may find their way past this seal, as the piston is repeatably cycled along the bore axis, and into the sterile fluids being injected into the patient, thereby potentially contaminating the patient.

The present invention has no vent between the sealed chamber and the exterior of the housing. The absence of such a vent ensures that no contaminant may find its way into the sealed chamber and thence into the unsealed chamber and the sterile fluid. Pressure management between the sealed chamber and the unsealed chamber is accomplished in other ways, as described above, such as membranes, gas accumulators, or initial pressure control.

The present approach thus achieves a fluid-capacitor effect while ensuring that external contaminants cannot enter through a vent and find their way into the unsealed chamber and thence into the sterile fluid in the next injection cycle. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIG. 4 is a sectional view of an injection valve with a syringe in the non-inserted position;

FIG. 5 is a sectional view like that of FIG. 4, with the syringe in the inserted position;

FIG. 6 is a sectional view taken along lines 6—6 of FIG. 4;

DETAILED DESCRIPTION OF THE INVENTION

Figure 1:
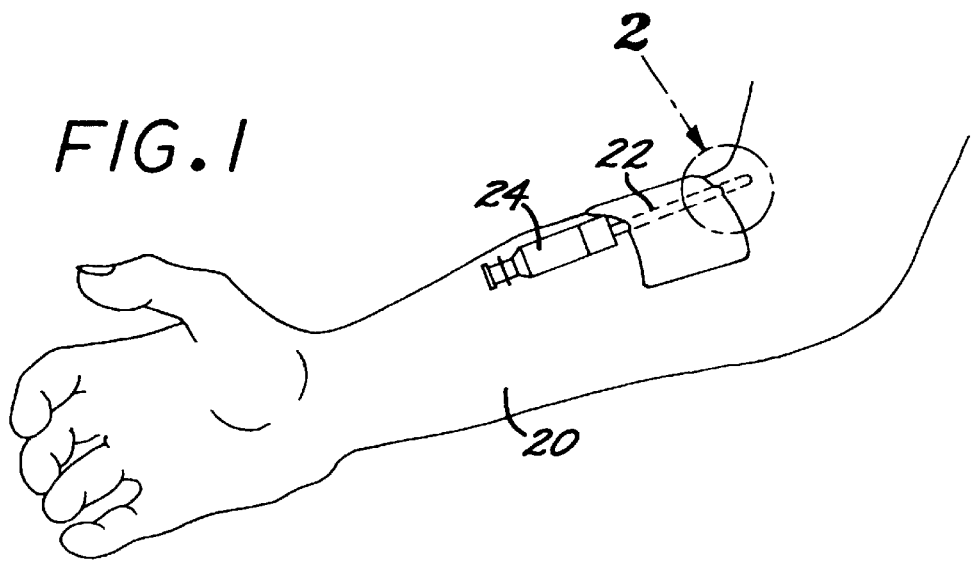
FIG. 1 is a perspective view of a catheter connected to a patient and an injection valve connected to the catheter.
Figure 2:
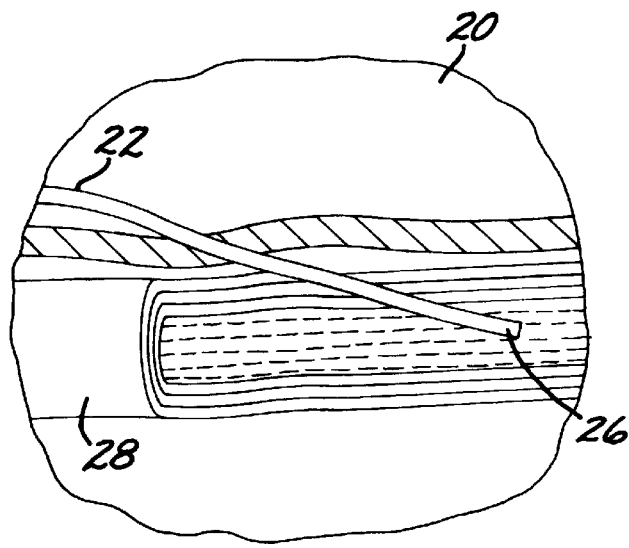
FIGS. 2–3 are sectional views of a catheter inserted into a vein, taken in region 2 of FIG. 1.
Figure 3:
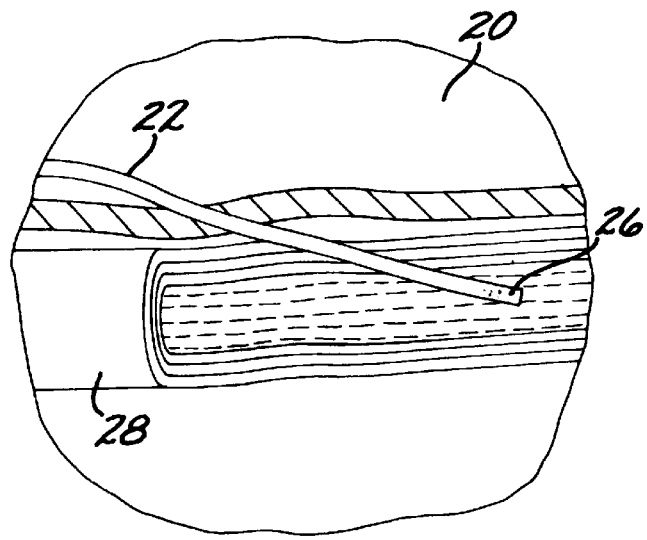

The present approach is used to inject fluids into a patient. FIG. 1 illustrates an arm 20 of a patient with a catheter 22 inserted into the arm. An injection apparatus 24 is attached to the catheter 22. FIGS. 2 and 3 illustrate a distal end 26 of the catheter 22 inserted into a vein 28 of the arm 20. When fluid is flowing from the injection apparatus 24 into the vein 28 through the catheter 22, no blood is drawn back into the catheter 22, FIG. 2. However, in some prior approaches to needle-free injection sites, when the injection is complete and the syringe is withdrawn from the injection apparatus so that a partial vacuum is created, blood may be drawn back into the catheter 22 and possibly into the injection apparatus 24. There is a resulting risk of blood coagulating in the catheter 22 and possibly in the injection apparatus 24, so that these components must be replaced with possible medical complications as well as additional discomfort, pain, and cost to the patient.

In one improved version of the injection apparatus, the contents of a fluid reservoir inside the injection apparatus 24 are expelled into the vein 28 by a spring-loaded piston when an injecting syringe is withdrawn from the injection apparatus 24, see for example U.S. Pat. No. 6,228,069. This action prevents blood from being drawn back into the catheter 22 and the injection apparatus 24 at the conclusion of the injection procedure. However, a portion of the interior of the injection apparatus 24 is vented to the exterior of the injection apparatus in order to prevent a buildup of excessive pressures on the spring side of the piston. There is a sliding seal around the edge of the piston, between the vented volume and the volume contacting the injected fluid. Although this sliding seal is operable from a fluid seal standpoint in the operation of the injection apparatus, there is no certainty that it prevents potential cross contamination of the injected fluid by fluid-borne or air-borne contaminants that find their way from the exterior of the injection apparatus 24, through the vent, into the vented volume, and across the seal into the injected sterile fluid.

The present approach is concerned with avoiding such potential clogging of the catheter and the injection apparatus from blood drawn back through the catheter 22, and at the same time avoiding potential contamination of the interior of the injection apparatus 24 due to contaminants external to the patient that find their way into the injection apparatus 24 through a vent.

Figure 7:
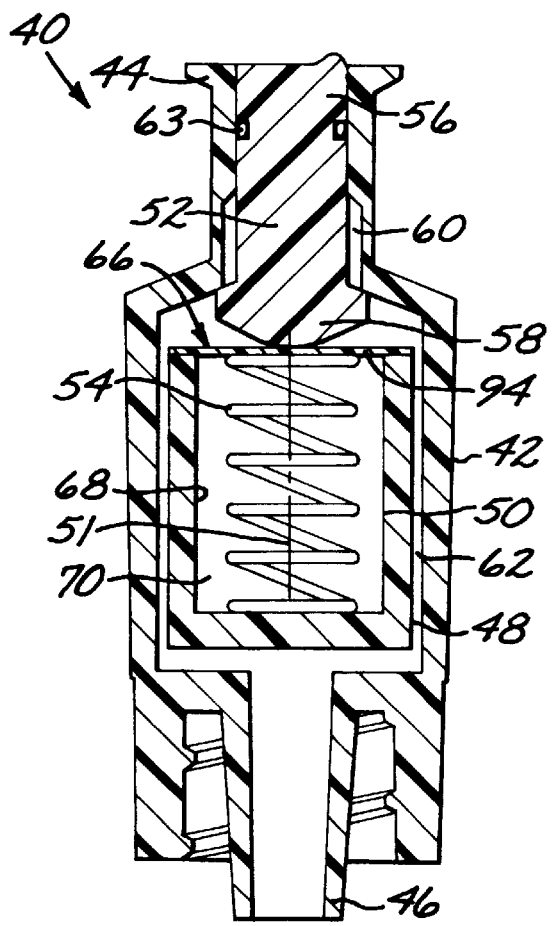
FIG. 7 is a sectional view of another embodiment of the invention, with no syringe present.

FIGS. 4–6 illustrate one embodiment of the present invention based on the embodiment found in FIGS. 6A, 6B, and 7 of the parent application Ser. No. 09/410,419. The description of the fundamental structure and operation is incorporated here. Briefly, an injection apparatus 40 (that may be used as the injection apparatus 24 of FIG. 1) includes a hollow housing 42 having an inlet 44, an outlet 46, and a fluid channel 48 extending between the inlet 44 and the outlet 46. A bore 50 within the housing 42 is closed at one end, the end remote from the inlet 44. In the illustrated embodiment, the bore 50 is substantially cylindrical with a bore axis 51, and the inlet 44 and the outlet 46 are coaxial along the bore axis 51. (In other embodiments, the outlet 46 need not be coaxial with the bore axis 51.) A piston 52 is slidable within the bore 50 between a first position (as seen in FIG. 4) relatively closer to the inlet 44 and a second position (as seen in FIG. 5) relatively farther from the inlet. The piston 52 is biased toward the first position by a spring 54, here illustrated as a coil spring.

The piston 52 has a first portion 56 and a second portion 58. The fluid channel 48 has a first length 60 (see FIG. 6) positioned adjacent to and radially outwardly from the first portion 56 of the piston 52, when the piston 52 is in the first position. The first length 60 of the fluid channel 48 controllably communicates with the inlet 44 when the piston 52 is in the second position. A second length 62 of the fluid channel 48 communicates between the first length 60 and the outlet 46. When the piston 52 is in the first position shown in FIG. 4, a piston inlet seal 63, preferably an O-ring seal extending around the first portion 56, seals between the inlet 44 and the first length 60 of the fluid channel 48. When the piston 52 is forced to the second position shown in FIG. 5 by the insertion of an end 64 of a (needleless) syringe, the axial movement of the first portion 56 of the piston 52 unseals the first length 60 of the fluid channel 48 by moving the piston inlet seal 63 below the top of the first length 60 of the fluid channel 48, allowing injected fluid to flow from the syringe, through the inlet 44, through the first length 60 and the second length 62 of the fluid channel 48, through the outlet 46 and thence to the patient through the catheter 22 that is attached to the outlet 46. The injection apparatus 40 thus acts as a needle-free valve.

A piston seal 66, which may be a sliding seal, between the second portion 58 of the piston 52 and a wall 68 of the bore 50 divides the bore 50 into a sealed chamber 70 (below the piston 52 in FIG. 4) and an unsealed chamber 72 (above the piston 52 in FIG. 5). In the preferred approach, the spring 54 is located within the sealed chamber 70. When the piston 52 is in the second position, new volume in the form of the unsealed chamber 72 within the bore 50 is created. The injection apparatus 40 with the new volume 72 acts as a needle-free valve fluid capacitor.

The unsealed chamber 72 is in communication with the fluid channel 48. When the piston 52 is moved to the second position shown in FIG. 5 for sterile fluid injection, a small amount of the fluid flows into the unsealed chamber 72. At the conclusion of the fluid injection as the end 64 of the syringe is withdrawn so that the piston 52 moves back toward the first position shown in FIG. 4, the fluid in the unsealed chamber 72 is expelled into the fluid channel 48. Because the movement of the piston 52 has sealed the inlet 44 from the fluid channel 48 as described above, the fluid expelled from the unsealed chamber 72 flows toward the outlet 46 and thence into the catheter 22 and in the direction toward the vein 28. The drawing of blood back into the catheter 22 is thereby prevented.

One concern is that the pressure in the sealed chamber 70 may become sufficiently large, when the piston is moved to the second position of FIG. 5, that the built-up pressure may interfere with the smooth operation of the piston 52 and thence of the injection apparatus 40. For this reason, some prior approaches have provided a vent to atmosphere of the sealed chamber 70 so as to avoid the pressure buildup. However, as discussed above, contamination may find its way from the exterior, through the vent, past the piston seal, into the unsealed chamber, and thence into the fluid channel where it contaminates the fluid within the injection apparatus 40. (The inlet 44 is readily accessible for cleaning, as with an alcohol swipe, to prevent any contamination through the inlet 44.)

The present inventors have recognized that the undesirable excessively high pressure may be avoided by any of several approaches, three of which are illustrated in relation to the embodiment of FIGS. 4–6. In the injection apparatus 40, there is no vent between the exterior of the housing 42 and the sealed chamber 70 (or the unsealed chamber 72) through any vent provided to prevent pressure buildup on the spring side of the piston.

The approaches illustrated in relation to the embodiment of FIGS. 4–6 fall into two primary categories: a gas volume separated from the exterior of the housing by a balloon membrane that serves to receive air expelled from the sealed chamber 70 as the piston 52 moves to the second position; and an internal gas accumulator.

A gas volume 80 is defined by a portion of the housing 42 and a balloon membrane 82. The gas volume 80 communicates with the sealed chamber 70 through a port 84. When the piston 52 is in the first position of FIG. 4, the balloon membrane 82 is collapsed and the gas volume 80 is small. When the piston 52 is moved to the second position of FIG. 5, air flows from the sealed chamber 70 through the port 84 and into the gas volume 80, expanding the balloon membrane 82. A wall 86 is provided to prevent the balloon membrane 82 from being inadvertently ruptured or damaged. This balloon membrane approach may be used wherever there is some available volume within or at the surface of the housing 42. The illustrated embodiment places the gas volume 80 near the outlet 46, but the gas volume may be on the lateral side of the housing, the lateral side of the bore so that the balloon membrane expands into the fluid flow channel 48, within the housing by removing housing material to define an available volume, within the unsealed chamber 72 (with the port being through the piston itself and with care taken to be certain that the balloon membrane does not interfere with the sealing action of the piston 52 to seal the inlet 44), or near the inlet 44. Care is taken so that the balloon membrane 82 does not negate the effect of the unsealed chamber in serving as the fluid capacitor.

In another approach, an internal gas accumulator 92 is provided. In the illustrated approach, the entire interior of the piston 52 is hollowed out to define the gas accumulator 92. Alternatively, gas accumulator volume may be provided within the wall of the housing 42. This approach differs from the balloon membrane approach described above in that there is no need for a membrane in the gas accumulator approach, because there is no communication between the sealed chamber 70 and the exterior of the housing 42 or the unsealed chamber 72. By adding a constant accumulator volume to the sealed chamber 70, the maximum value of the pressure experienced in the sealed chamber when the piston is in the second position is reduced, as compared with the maximum pressure in the absence of the accumulator volume.

Figure 8:
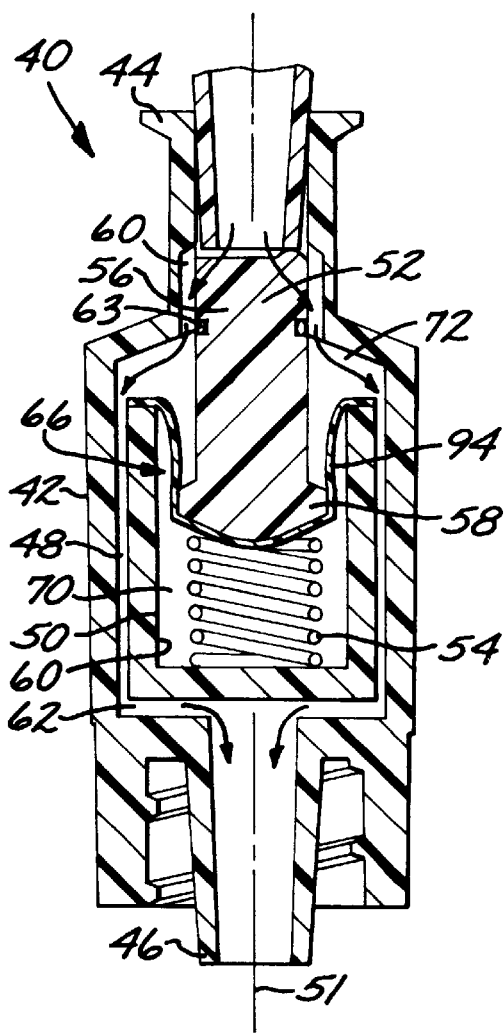
FIG. 8 is a sectional view like that of FIG. 7, with the syringe in the inserted position.

FIGS. 7–8 illustrate another approach. The basic operation of the embodiment of the injection apparatus 40 of FIGS. 7–8 is like that discussed above, and the prior description is incorporated here. In this case, the piston seal 66 is a flexible membrane seal 94. As the piston 52 moves from the first position of FIG. 7 toward the second position of FIG. 8 to increase the gas pressure within the sealed chamber 70, the membrane seal 94 bulges into the unsealed chamber 72 to relieve the pressure within the sealed chamber 70. Care is taken that the membrane seal 94 in its bulged state does not fill the unsealed chamber 72 and negate its fluid capacitor functionality.

In yet another approach, any of these ventless structures may be assembled such that a gas pressure within the sealed chamber 70 is less than a gas pressure within the unsealed chamber 72, when the piston 52 is in its first position. This state may be achieved by assembling the injection apparatus 40 and completing the piston seal 46 with the injection apparatus 40 in a reduced-pressure environment such as a partial vacuum chamber or at high altitude. By reducing the pressure in the sealed chamber 70 with the piston 52 in the first position, the pressure within the sealed chamber 70 with the piston 52 in the second position is not as great as it would be otherwise.

In the embodiments of FIGS. 4–8 the unsealed chamber 72 defined between the piston 52 and the housing 42 serves as the fluid reservoir. The separate fluid channel 48, positioned between the inner wall and the outer wall of the housing 42, provides the fluid flow path between the inlet 44 and the outlet 46. This separation of structure, between the unsealed chamber 72 and the fluid channel 48, and function are significant, because they permit the inlet 44 and the outlet 46 to be coaxial with the bore axis 51. In an alternative possible design wherein the fluid flow channel serves as the fluid reservoir as well, and there is no unsealed chamber, the outlet must be placed on the side of the housing. This placement of the outlet is highly undesirable and cumbersome for some medical applications.

The embodiments of FIGS. 4–8 illustrate these several approaches. The various structural approaches may be used by themselves or in any combination, and in combination with the reduced-pressure approach.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. An injection valve comprising:
    a housing having an inlet, an outlet, and a fluid channel extending between the inlet and the outlet;
    a bore within the housing;
    a piston slidable within the bore between a first position and a second position and biased toward the first position, the piston closing and sealing the inlet when the piston is in the first position and allowing fluid to pass from the inlet to the fluid channel to the outlet when the piston is in the second position; and
    a piston seal between the piston and a wall of the bore, the piston seal dividing the bore into a sealed chamber and an unsealed chamber, there being no vent between the sealed chamber and an exterior of the housing.

2. The injection valve of claim 1, wherein the bore is substantially cylindrical with a bore axis, and wherein the inlet and the outlet are coaxial along the bore axis.

3. The injection valve of claim 1, wherein the piston seal is a sliding seal.

4. The injection valve of claim 1, wherein the piston seal is a diaphragm seal.

5. An injection valve comprising:
    a housing having an inlet, an outlet, and a fluid channel extending between the inlet and the outlet;
    a bore within the housing, the bore having a closed end;
    a piston slidable within the bore between a first position wherein the piston is relatively far from the closed end and a second position wherein the piston is relatively near to the closed end, the piston closing and sealing the inlet when the piston is in the first position and allowing fluid to pass from the inlet to the fluid channel to the outlet when the piston is in the second position;
    a biasing spring that biases the piston toward the first position; and
    a piston seal between the piston and a wall of the bore, the piston seal dividing the bore into a unsealed chamber and a sealed chamber adjacent to the closed end, there being no vent between the sealed chamber and an exterior of the housing.

6. The injection valve of claim 5, wherein the bore is substantially cylindrical with a bore axis, and wherein the inlet and the outlet are coaxial along the bore axis.

7. The injection valve of claim 5, wherein the piston seal is a sliding seal.

8. The injection valve of claim 5, further including
    a deformable membrane having a first side in communication with the sealed chamber, the deformable membrane being deformable responsive to gas pressure changes within the sealed chamber.

9. The injection valve of claim 5, further including
    a gas accumulator communicating with the sealed chamber.

10. The injection valve of claim 5, wherein a gas pressure within the sealed chamber is less than a gas pressure within the unsealed chamber, when the piston is in its first position.

11. An injection valve comprising:
    a housing having
        a body,
        an inlet tube at a first end of the body,
        an outlet tube at a second end of the body remote from the first end, and
        a fluid channel extending through the body and between the inlet tube and the outlet tube;
    a bore within the housing, the bore having a bore axis and a closed end adjacent to the second end of the body, wherein the inlet tube is coaxial with the bore axis;
    a piston having
        a first axial segment coaxial with the bore axis and slidable within the bore between a first position wherein the first axial segment is relatively far from the closed end and a second position wherein the first axial segment is relatively near to the closed end, and
        a second axial segment coaxial with the bore axis and remote from the closed end of the bore, the second axial segment closing and sealing the inlet tube when the first axial segment is in the first position and allowing fluid to pass through the inlet tube and into the fluid channel when the first axial segment is in the second position;
    a biasing spring that biases the piston toward the first position; and
    a piston seal between the first axial segment of the piston and a wall of the bore, the piston seal dividing the bore into a unsealed chamber and a sealed chamber adjacent to the closed end, there being no vent between the sealed chamber and an exterior of the housing.

12. The injection valve of claim 11, further including a deformable membrane having a first side in communication with the sealed chamber, the deformable membrane being deformable responsive to gas pressure changes within the sealed chamber.

13. The injection valve of claim 11, further including a gas accumulator communicating with the sealed chamber.

14. The injection valve of claim 11, wherein the inlet tube is sized to receive a syringe tip therein.

15. The injection valve of claim 11, wherein a transverse end of the first axial segment remote from the closed end of the piston has a bump thereon.

16. The injection valve of claim 11, wherein a gas pressure within the sealed chamber is less than a gas pressure within the unsealed chamber, when the piston is in the first position.

* * * * *